US009555256B2

(12) United States Patent
Jullien et al.

(10) Patent No.: US 9,555,256 B2
(45) Date of Patent: Jan. 31, 2017

(54) METHOD OF MAKING A CONNECTOR HEAD OF A MULTIPOLAR LEAD OF AN ACTIVE IMPLANTABLE MEDICAL DEVICE

(75) Inventors: Elodie Jullien, Dardilly (FR); François Lucas, Montrouge (FR)

(73) Assignee: SORIN CRM SAS, Clamart (FR)

( * ) Notice: Subject to any disclaimer, the term of this patent is extended or adjusted under 35 U.S.C. 154(b) by 634 days.

(21) Appl. No.: 13/606,435

(22) Filed: Sep. 7, 2012

(65) Prior Publication Data
US 2013/0065443 A1 Mar. 14, 2013

(30) Foreign Application Priority Data

Sep. 8, 2011 (FR) ..................... 11 57994

(51) Int. Cl.
| | | |
|---|---|---|
| B28B 7/22 | (2006.01) | |
| A61N 1/375 | (2006.01) | |
| B29C 45/16 | (2006.01) | |
| H01R 13/52 | (2006.01) | |
| H01R 24/58 | (2011.01) | |

(Continued)

(52) U.S. Cl.
CPC ......... *A61N 1/3752* (2013.01); *B29C 45/1671* (2013.01); *B29C 45/1676* (2013.01); *H01R 13/5224* (2013.01); *H01R 24/58* (2013.01); *H01R 43/24* (2013.01); *B29C 45/14065* (2013.01); *B29C 45/14639* (2013.01); *B29C 2045/1664* (2013.01); *B29C 2045/1678* (2013.01); *B29L 2031/36* (2013.01); *B29L 2031/753* (2013.01); *H01R 24/76* (2013.01); *H01R 2201/12* (2013.01); *Y10T 29/49117* (2015.01)

(58) Field of Classification Search
CPC .. B29C 45/16; B29C 45/1615; B29C 45/1676; H01R 13/5224; H01R 24/58; H01R 43/24
See application file for complete search history.

(56) References Cited

U.S. PATENT DOCUMENTS

| | | |
|---|---|---|
| 7,175,478 B2 | 2/2007 | Ollivier |
| 7,630,768 B1 | 12/2009 | Coffed et al. |

(Continued)

FOREIGN PATENT DOCUMENTS

| | | |
|---|---|---|
| EP | 1641084 A1 | 3/2006 |
| EP | 2228096 A2 | 9/2010 |

OTHER PUBLICATIONS

FR, Foreign Search Report (Annexe Au Rapport De Recherche Preliminaire Relatif A La Demande De Brevet Francais No. FR 1157994 FA 755110), Mar. 6, 2012.

*Primary Examiner* — Joseph S. Del Sole
*Assistant Examiner* — John Robitaille
(74) *Attorney, Agent, or Firm* — Foley & Lardner LLP (57) ABSTRACT

Forming a connector head for a generator of an active implantable medical device by providing a pin (20) having alternating smooth sections (21) for receiving an electrical contact (210) and a profiled section (22); disposing the electrical contacts on the smooth sections; injecting into a first mold a flexibly resilient material around the profiled sections of the pin to produce isolation elements between the electrical contacts; injecting in a second mold a rigid material around the pin to form the connector head with the electrical contacts and isolation elements embedded therein; and withdrawing the pin from the cavity of the connector head thus formed. The material provides precise axial and radial positioning of the different elements, and good electrical insulation.

13 Claims, 6 Drawing Sheets

(51) Int. Cl.
*H01R 43/24* (2006.01)
*B29L 31/00* (2006.01)
*B29L 31/36* (2006.01)
*B29C 45/14* (2006.01)
*H01R 24/76* (2011.01)

(56) References Cited

U.S. PATENT DOCUMENTS

| | | |
|---|---|---|
| 2007/0225772 A1 | 9/2007 | Lahti et al. |
| 2008/0234778 A1 | 9/2008 | Rebentisch |
| 2009/0017700 A1 | 1/2009 | Zart et al. |
| 2009/0118778 A1 | 5/2009 | Biggs, Jr. et al. |

FIG-1

FIG_3

FIG_4a

FIG_4b

FIG-5

METHOD OF MAKING A CONNECTOR HEAD OF A MULTIPOLAR LEAD OF AN ACTIVE IMPLANTABLE MEDICAL DEVICE

RELATED APPLICATION

The present application claims the priority date benefit of French Patent Application No. 11/57994 entitled "Method Of Making A Connector Head Of A Multipolar Lead Of An Active Implantable Medical" and filed Sep. 8, 2011, which is hereby incorporated by reference in its entirety.

FIELD OF THE INVENTION

The present invention relates to active implantable medical devices as defined by the Jun. 20, 1990 directive 90/395/CEE of the European Community Council, including those implanted devices that continuously monitor the cardiac rhythm of a patient and deliver, if and as necessary, to the heart electrical pulses for cardiac stimulation, cardiac resynchronization ("CRT"), cardioversion and/or defibrillation in response to a rhythm disorder detected by the device. It also includes devices such as cochlear implants, drug pumps, implanted biological sensors, etc. More particularly, the present invention relates to manufacturing connector heads that are the interface between the device and external leads and/or sensors.

BACKGROUND

Active Implantable medical devices generally comprise a housing, designated a "generator", that is electrically and mechanically connected to one or more "leads" provided with electrodes intended to come into contact with the patient's tissues where it is desired to apply stimulation pulses and/or to collect an electrical signal: e.g., the myocardium, nerve, and/or muscle tissue.

There are standardized connection systems to ensure the interchangeability of leads and generators that are produced by different manufacturers. Thus, the standards called "IS-1" and "IS-4" define a number of dimensional and electrical characteristics related to leads used for cardiac pacing and cardiac resynchronization therapy ("CRT"). For defibrillation leads, wherein the electrical stresses are more severe given the higher energy pulses to be conducted from the generator to the lead, the standards known as "DF-1" and "DF-4" apply and define the dimensional and electrical characteristics for that system connection.

The complexity of these leads, which already incorporate the specific constraints in terms of electrical energy associated with the particular use, pacing or shock, is increased with the development of multisite devices and intracardiac sensors, such as endocardial acceleration sensors (EA). As a result, in terms of connectivity, there is a growing number of connection plugs, and moreover different standards depending on the plugs.

The benefit brought by a single plug, subject to a single standard, with a plurality of electrical contacts to ensure simultaneously connections to various terminals of the generator for all energy levels, whether for the collection of depolarization signals, for the application of stimulation pulses or for the delivery of defibrillation shock energy, can be understood.

In this context, it is known to have a single "isodiameter" plug connection, that is to say, with a uniform cylindrical shape, for insertion in a counterpart cylindrical cavity of the connector head of the generator. EP 1641084 A1 and its counterpart U.S. Pat. No. 7,175,478 B1 (both assigned to Sorin CRM S.A.S., previously known as ELA Medical) describes such an isodiameter connection plug, with the outer cylindrical surface having a stack of annular electrical contact areas, made of conductive cylindrical rings, and insulating cylindrical zones providing electrical insulation between the conductive rings. To receive such a multipolar connection plug and to connect it to the electrical generator, the connector head of the generator must have a cavity formed similarly (complementary) to the plug itself, in that it also includes a stack of annular electrical contact elements to make electrical contact with the corresponding conductive rings of the connection plug. In this stack, the annular electrical contact elements are alternately separated by annular isolation elements, provided on their inner diameter of sealing rings having a given profile, for application of a radial compression on the insulating cylindrical zones of the connection plug.

Note that, unlike the older embodiments wherein the isolation elements are carried by the lead, they are now arranged in the cavity, which has the advantage of providing new isolation elements each time the generator is replaced.

The term "isolation" used herein applies to both (i) the sealing of the cavity relative to the external environment, vis-à-vis in particular body fluids, and (ii) the electrical insulation, that is to say the low-voltage insulation of the electrical contact areas and elements, as well as the high-voltage insulation of the cavity with the outside environment.

U.S. Pat. Publication No. 2008/0234778 A1 describes a process for producing a connector head, with a silicone resilient monobloc part, extending all along the cavity. This silicone part is molded around a central pin of appropriate shape. To withdraw the pin after reticulation of the silicone, the part is dipped into a bath of n-heptane, which has the effect of swelling the silicone and radially expands the part, then allowing the withdrawal of the molding pin. This expanded state is also used to insert by the central cavity thus released the electrical contact elements, in housings provided in the silicone part. After evaporation of n-heptane, the silicone part resumes its original definitive dimensions, with the electrical contact elements embedded in it. But, because of the flexibility of the elastomer material, it is capable of compression and relaxation and this known method does not guarantee either the coaxiality of electrical contact elements with the isolation elements, or their axial positioning.

Similarly, EP 2228096 A2 and U.S. Pat. Publication No. 2009/0017700 A1 propose a method for producing an elastomer or epoxy connector head, the cavity of which includes elastomer seals. The electrical contacts are interposed between the seals of the cavity through side windows formed in the connector head, which does not control the coaxiality of the electrical contacts with the elastomer seals or their axial positioning. Moreover, the problem of isolation—sealing and electrical insulation—at the interface of elastomer seals and the head is not resolved.

U.S. Pat. No. 7,630,768 B1 and U.S. Pat. Publication No. 2009/0118778 A1 disclose methods for producing a molded connector head in a hard resin (typically polyurethane), to position and assembly, in a very precise and reliable method, electrical contact elements. However, they do not address in any way the implementation of flexible sealing elements, nor the isolation problems of isolating electrical contact elements from each other and from their environment, and sealing of the cavity, in particular from the body fluids.

OBJECT AND SUMMARY

It is, therefore, an object of the present invention to provide a method for producing a connector head that ensures, in a simple and economic method, the coaxiality of electrical contact and isolation elements, as well as the axial positioning of the isolation elements.

Broadly, the present invention is directed to a method of producing by dual-injection a connector head for a generator of an active implantable medical device, the connector head comprising a substantially cylindrical cavity for reception on the one hand of a multipolar lead of the device and having, on the other hand, alternating annular electrical contact elements and annular isolation elements with an inner sealing profile. In one embodiment, the dual-injection method comprises the steps of:

Providing a cylindrical pin having a diameter substantially equal to the diameter of the cavity, the pin alternatively having smooth sections for receiving the annular electrical contacts, and profiled sections having a profile that is a conjugate of the sealing profile of the annular isolation elements to be implemented;

Arranging the electrical contact elements on the smooth sections of the pin spaced apart axially to leave between the electrical contact elements an interval corresponding to said profiled sections of the annular isolation elements;

Injecting in a first mold a first material around the profiled sections to form the annular isolation elements, the first material being an elastic material having a first hardness;

Injecting in a second mold a second material, around the pin so as to form the connector head, the second material having a second hardness greater than the first hardness; and Axially releasing the pin from the cavity of the connector head thus obtained.

It should be understood by a person of ordinary skill in the art that, because of their pre-positioning directly on the smooth sections of the pin, the annular electrical contact elements (also called, more simply, the "electrical contacts") are perfectly concentric to the annular isolation elements (also called "seals") after the latter have been made by injection in the first mold around the profiled sections of the pin constituted of the first material, also called "flexible material" or "resilient material".

The coaxiality thus obtained according to the injection of the flexible material is maintained, as a result of the injection of the second material of higher hardness, or "rigid material", wherein the electrical contact elements remain anchored even when the pin is axially released by elastic deformation of the flexible material constituting the sealing profiles of the seals. These sealing profiles are designed so as to apply a radial compression on the insulating areas of the connection plug, thus ensuring the sealing of the connector vis-à-vis the body fluids, while also contributing to the electrical insulation between two poles of the plug.

In one embodiment, the first material has hardness less than 80 Shore A. It may be an elastomer material, in particular a silicone compound, or a thermoplastic polymer, especially thermoplastic polyurethane.

In one embodiment, the second material has a hardness greater than or equal to 70 Shore D. It may be a thermoplastic polymer, in particular thermoplastic polyurethane.

It should be understood that the first and second materials are biocompatible materials.

Advantageously, the method of the present invention provides a perfect axial positioning of the seals, which is definitively determined by the position of the profiled sections along the pin. After the injection of the second material, the axial positioning is retained by adhesion of the flexible material attached in the rigid material of the connector head.

Advantageously, the present invention offers many other benefits. In particular, its industrial implementation is facilitated by the reduction of the number of parts to be assembled. Indeed, it is not necessary to separately manufacture the seals and then assemble them in the connector head. Rather, in accordance with the present invention, they are directly incorporated into the cavity by the dual-injection of the first and second materials. The present invention therefore provides both the elasticity of the seals and the stiffness of the outer shape of the connector head. It also should be noted that the sealing profiles carried by the seals are directly formed on the pin of the mold during the dual-injection process.

In addition, one can observe that the overall volume of the cavity can be reduced with the various elements of the connector head being directly integrated into the cavity or molded together.

Finally, during dual-injection, the biocompatible materials adhere to each other so as to obtain an adhesion zone to ensure a sealing with respect to the external environment, and an insulation between the electrical contacts and between the electrical contacts and the external environment.

In one embodiment, the process of the invention comprises a step of, prior to injection of the first material, forcing the electrical contact elements to be in a determined axial position on the smooth sections of the pin, using a positioning tool, this position being maintained during the injection steps. Advantageously, this enables the electrical contacts to be in the required position within the cavity. Preferably, a perfect axial positioning of the electrical contacts is obtained by this method, which results, on the one hand, from the fact that during the first injection the electrical contacts are perfectly spaced along the pin through use of the positioning tool, and, on the other hand, from the fact that the electrical contacts are permanently anchored in the cavity during the second injection of the rigid material.

In one embodiment, the positioning tool comprises annular grooves formed on the outer diameter of the electrical contact elements and elements for wedging the electrical contact elements in position to match with the annular grooves.

Preferably, the first injection mold is dimensioned such that the outside diameter of the isolation elements is less than the outside diameter of the electrical contact elements. This results, after the second injection, in the electrical contacts being framed at their external diameter between two walls of rigid material, which ensures excellent locking in the axial direction and thus maintaining of their initial axial positioning.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

With reference to the drawings FIGS. 1-6, preferred embodiments of the method forming a connector head in accordance with the present invention will now be described. It should be understood that the attached drawings are given as non-limiting examples.

Figure 1:
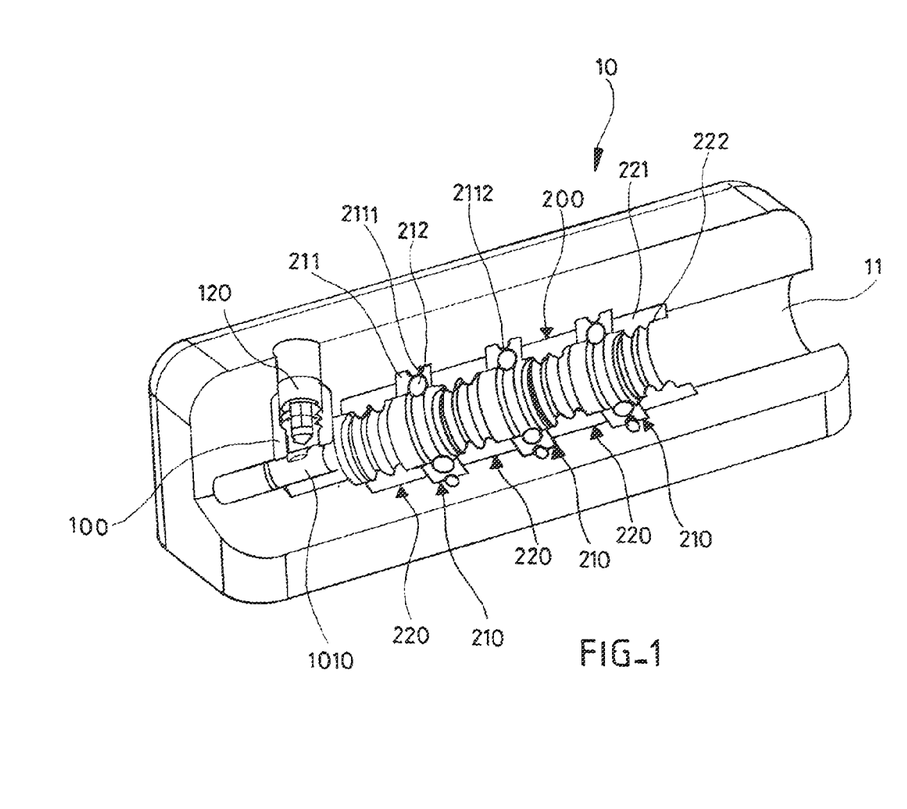
FIG. 1 is a perspective view of a connector head manufactured according to the method of the present invention.

Referring to FIG. 1, a connector head 10 for a generator of an active implantable medical device is shown. The connector head 10 comprises a substantially cylindrical cavity 11 for receiving, in accordance with the IS-4/DF-4 standard (ISO 27186-2010), a connection plug of a multipolar lead (not shown) so as to couple electrical signals between the generator of the device and, e.g., the heart of a patient.

EP 1641084 A1 and its counterpart U.S. Pat. No. 7,175, 478 (Sorin CRM S.A.S.) describes an example of one such quadripolar connection plug, which description is incorporated herein by reference. Specifically, this connection plug is of the prior art and is an isodiameter one, having at one end thereof an axial electrical contact pin and, on the body of the plug, three annular electrical contact zones made by conductive cylindrical rings. The electrical contact zones are alternately separated by intercalary insulating cylindrical zones to electrically isolate the electrical contact areas from one another.

One can thus, in a single motion insert the connection plug into cavity 11 of head 10, simultaneously to perform all the necessary electrical connections between the generator and the poles of the connection plug.

For this purpose, cavity 11 must of course be provided with elements homologous to those present on the connection plug. These elements will now be described in detail in connection with the above referenced standard.

As shown in FIG. 1, cavity 11 of head 10 comprises a threaded screw insert 100 that is used to hold the connection plug in cavity 11. In this regard, a screw 120 is inserted into screw insert 100 and tightened against the axial pin of the connection plug (not shown), after the axial pin has been fully inserted in a socket 1010. This obtains a secure electrical connection between the axial pin and the generator. Cavity 11 includes alternating electrical contact and isolation elements (collectively an "alternation" 200).

More specifically, alternation 200 comprises three annular electrical contact elements 210, provided for making electrical contact with the corresponding conductive rings of the connection plug in order to transmit, with the axial pin, all high/or low voltage electrical signals from the electronics of the generator to the heart via implanted multipolar lead, and vice versa. Electrical contact elements (or "electrical contacts") 210 should be able to receive the connection plugs of the leads and meet the insertion and extraction force, as well as the electrical performance requirements defined in the above referenced (or other applicable) standard.

With reference still to FIG. 1, electrical contacts 210 are composed of two annular cylindrical sub-elements, namely a cage 211 made of a biocompatible material such as stainless steel, e.g., type MP35N, and a spring contact 212 received by cage 211 within a groove 2111 formed in its internal surface part, along the inside diameter. Spring contact 212 is preferably a cylindrical spring. More preferably, it is a single piece of implantable resilient metal and performs a function of making a resilient contact with the conductive rings of the connection plug of the lead, so as to obtain the best electrical contact with a low contact resistance.

The outer diameter of cage 211 forms an electrical connection zone or pad for the wire connecting spring contacts 212 to the electronics of the generator. Such an electrical connection is generally made by laser or electrical welding.

With reference to FIG. 1, electrical contacts 210 are alternately separated along the alternation 200 by annular isolation elements (or "seals") 220 that are disposed to be opposite the insulating areas of the connection plug, so to create electrical isolation between the electrical contacts 210 and to carry out the electrical insulation and sealing of the cavity 11 vis-à-vis the external environment. Isolation elements 220 must also guarantee high-voltage insulation and remove the leakage paths at the inner diameter with the isolating zones of the connection plug as well as at their outside diameter, at the interface with the cavity 11.

As shown in FIG. 1, seals 220 are formed of a seal body 221 made of an elastic biocompatible material, such as a silicone elastomer, of hardness less than 80 Shore A. The inner annular face of seal body 221 carries a sealing profile 222, in the preferred embodiment consisting of two rings that provide radial compression against an insulating region of the connection plug when the latter is inserted into connector head 10, thus ensuring sealing of cavity 11 and the insulation between two consecutive conductive rings of the connection plug and of corresponding spring contacts 212.

All electrical contact and isolation elements described above are embedded together in head 10 of the connector itself, made of a material of greater hardness than the elastic material of seals 220, such as a thermoplastic polyurethane having hardness greater than or equal to 70 Shore D. To make head 10 of the connector of FIG. 1, the invention provides a method for implementing a molding of a pin 20, shown in FIGS. 2*a* and 2*b*.

Figures 2A, 2B:
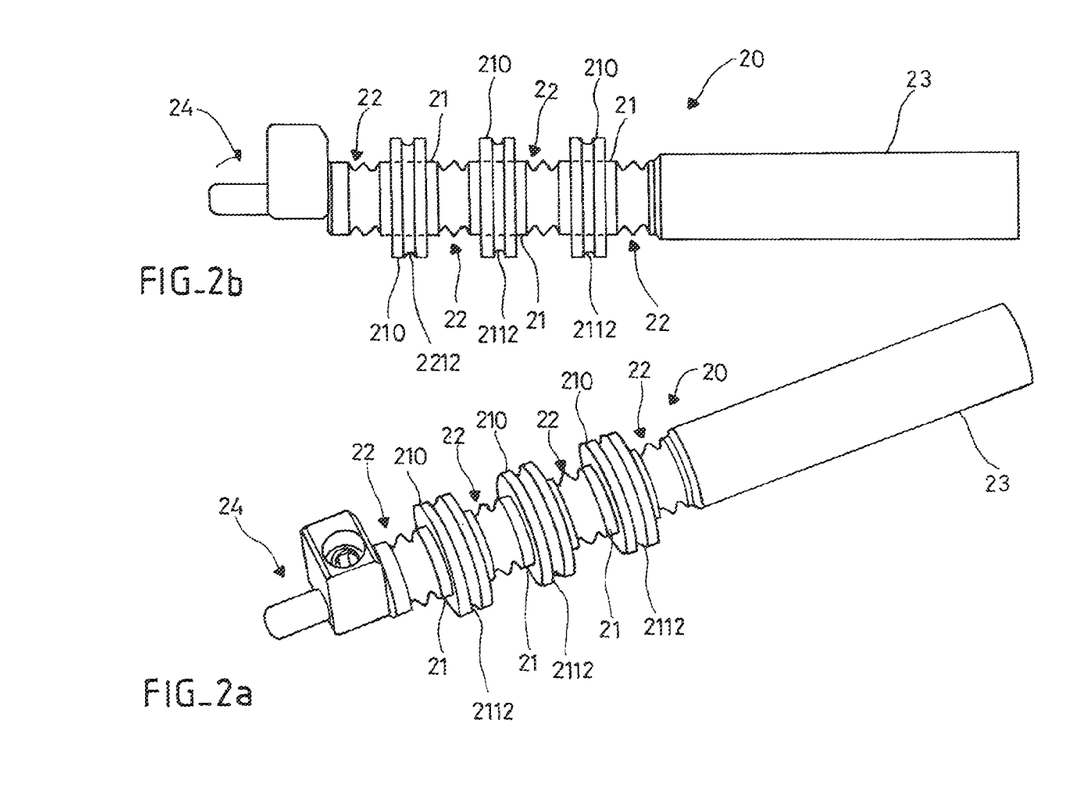
FIG. 2*a* is a perspective view of a pin with four electrical contacts used in the method of the present invention.
FIG. 2*b* is a side view of the pin of FIG. 2*a*.

With reference to FIGS. 2*a* and 2*b*, pin 20 is preferably constructed with a generally cylindrical shape having a diameter substantially equal to that of the cavity 11, and is segmented into a plurality of sections associated with different functional elements of cavity 11. The proximal end 23 of pin 20 corresponds to the input end of cavity 11, while distal end 24 is equipped with the components necessary for molding of the screw insert 100. The portion of pin 20 between its proximal end 23 and its distal end 24 is divided into an alternation of smooth sections 21 and profiled sections 22. Smooth sections 21 correspond to electrical contacts 210 described above which will be disposed thereon. With reference to FIG. 1, profiled sections 22 preferably have a profile 222 that is complementary to the sealing profile of seals 220.

Figure 3:
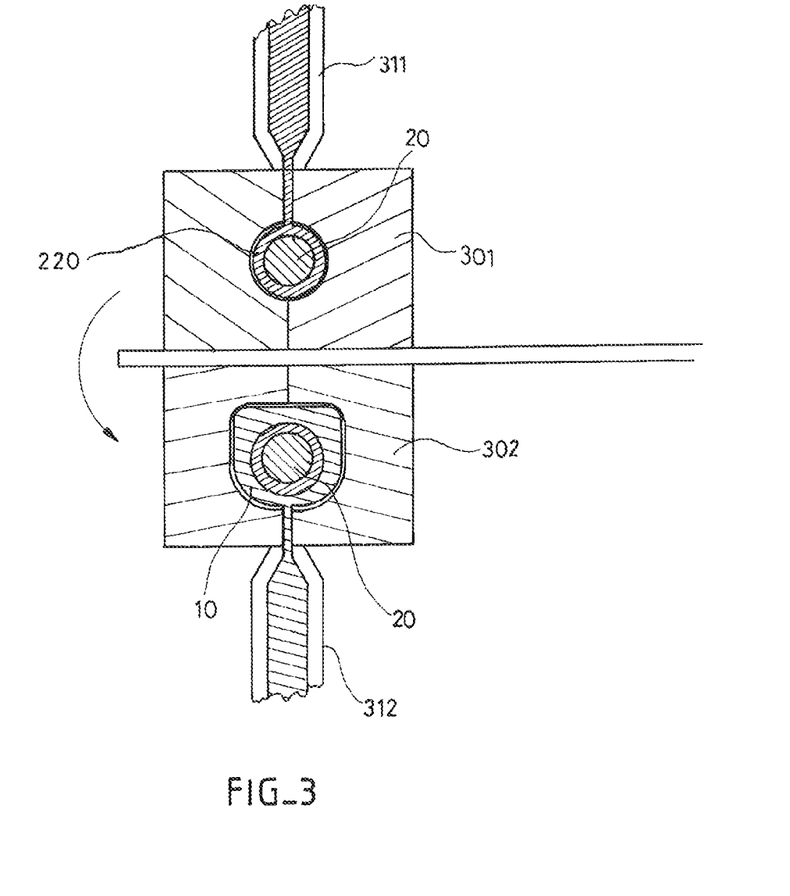
FIG. 3 is a sectional view illustrating the steps of molding in accordance with a first preferred embodiment of the present invention.
Figure 4A:
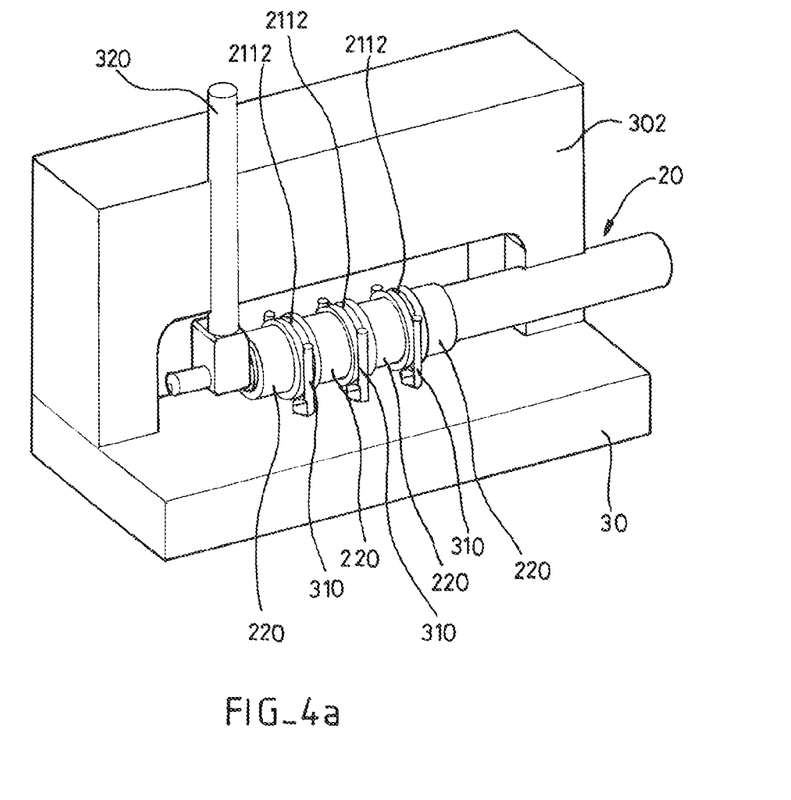
FIG. 4*a* is a perspective sectional view illustrating the second molding step in accordance with a first preferred embodiment of the present invention.
Figure 4B:
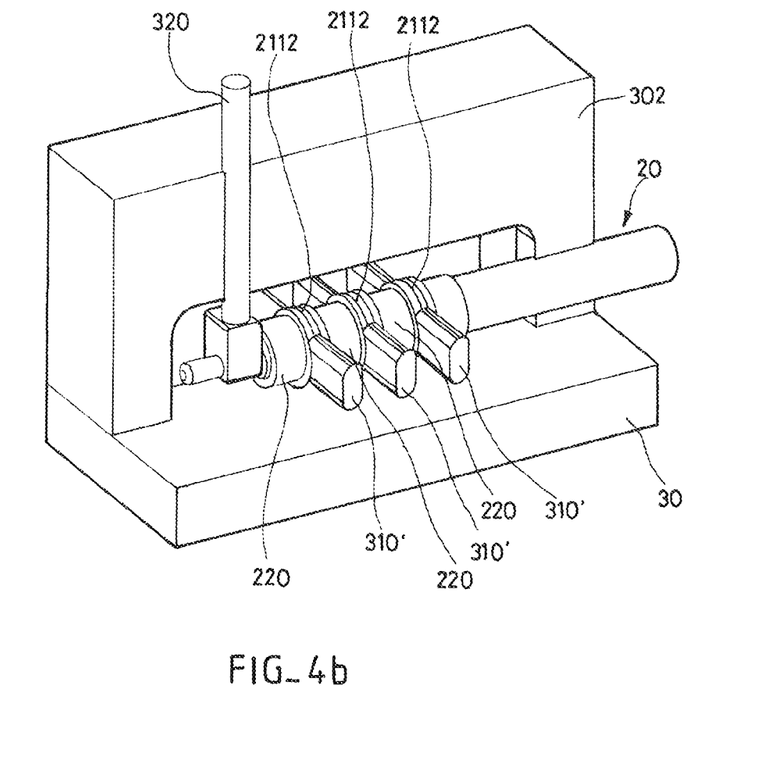
FIG. 4*b* is a perspective sectional view illustrating a second molding step in accordance with a second preferred embodiment of the present invention.

Pin 20 thus formed is placed on a plate 30 for injection molding (see e.g., FIGS. 4a and 4b). This placement involves using a positioning tool having members for wedging in position electrical contacts 210, to match with annular grooves 2112 formed on the outer diameter of electrical contacts 210. These positioning tool wedging members thus axially position electrical contacts 210 along the pin 20. In FIG. 4a, for example, the wedging members are constituted by vertical rods 310 fixed to plate 30 being inserted into the grooves 2112; FIG. 4b shows an alternative embodiment in which wedging members 310' are horizontal lugs also matching with peripheral grooves 2112 of electrical contacts 210. Pin 20 as thus fitted with wedging members is locked into a first mold 301 that can be seen in FIG. 3.

With reference to FIG. 3, the axial positioning tools are not shown. This first molding step is intended to form seals 220 by an injection of a resiliently flexible material around the profile sections 22 of pin 20, through a nozzle 311. The resiliently flexible material may, for example, be a biomedical polymer as a Elast-Eon or ECSil (trademarks) of Aor-Tech Biomaterials, of hardness less than 80 Shore A. This provides pin 20 with seals 220 as shown in FIG. 4a.

It should be understood that at this stage of the process, the coaxial alignment of electrical contacts 210 with seals 220 is guaranteed from the fact that these elements are carried by the same molding pin 20. The correct axial positioning of the seals 220 along pin 20 is assured by the position defined by the profiled sections on pin 20. Similarly, the axial positioning of the electrical contacts 210 is perfectly controlled by using the positioning tools and pin 20 described above.

Also it should be understood that with each seal/electrical contact interface, the polymerization of the flexible resilient material creates in a radial plane a tight connection between the seal 220 and the corresponding lateral side of electrical contact 210. This later prevents, when over-molding of the assembly by a rigid material, any penetration of the material between the electrical contact 210 and the seal 220, which otherwise could create a leakage and electrical breakdown path between adjacent electrical contacts.

With reference to FIG. 3, mold 301 for injection of the first resiliently flexible material is then replaced by a mold 302 into which the second rigid material to form cavity 11 and head 10 of connector is injected through nozzle 312. This rigid material may, for example, be an Elast-Eon or ECSil, of hardness greater than or equal to 70 Shore D.

FIGS. 4a and 4b show in greater detail the installation of pin 20 into mold 302. A rod 320 is screwed on the components of the insert molding components 100 and intended to create a protected zone for the subsequent introduction of tightening screw 120.

Figure 5:
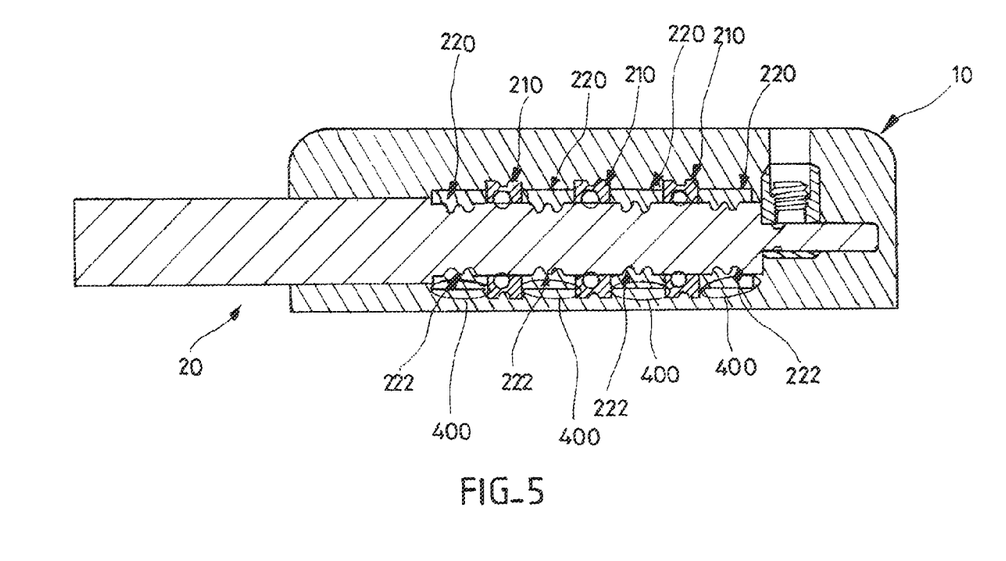
FIG. 5 is a cross-sectional view of a connector head resulting from the second molding step according to FIGS. 4*a* and 4*b*.

After removal of mold 302 and rods 320, connector head 10 is as obtained as shown in FIG. 5 (pin 20 is still present). One can see from this figure that the axial positioning of seals 220 is permanently fixed, to the extent they are embedded (i.e., anchored) in the rigid material of head 10.

Similarly, electrical contacts 210, are maintained in axial position due to the fact that each electrical contact is clamped between two walls of rigid material. To obtain this result, the first mold 301 is dimensioned so that the outside diameter of the seals 220 is smaller than the outside diameter of the electrical contacts 210. Pin 20 can be released from cavity 11 by an elastic deformation of sealing rings 222.

Note that wedging elements 310, 310' of electrical contacts 210 remain in place during the second molding step providing the rigid material. They are then laterally removed, which leaves windows that, in the case illustrated in FIG. 4b, are filled by silicone injection. In the alternative case illustrated in FIG. 4a, rods 310 are used to produce the electrical contact made with the conductive rings of the connection pin.

Finally, one can observe in FIG. 5 the formation of adhesion zones 400, preferably a chemical adhesion at the interface between the resiliently elastic and rigid materials injected: These zones 400 ensure isolation—a sealing from the external environment and between electrical contacts and the environment by providing an insulation barrier to leakage current.

One skilled in the art will appreciate that the present invention may be implemented by embodiments other than those described above, which are provided for purposes of explanation and illustration, and not of limitation.

The invention claimed is:

1. A process for producing a connector head for a generator of an active implantable medical device, the connector head including a substantially cylindrical cavity for reception of a multipolar lead, said cavity comprising an alternation of annular electrical contact elements and annular isolation elements, said annular isolation elements having an inner sealing profile, comprising:

providing a cylindrical pin having a diameter substantially equal to the diameter of the cavity, said pin having alternately smooth sections for receiving a plurality of annular electrical contact elements, and profiled sections having a profile that is a complement of said inner sealing profile;

arranging said annular electrical contact elements on said smooth sections of the pin while axially leaving an interval between said annular electrical contact elements, said interval corresponding to said profiled sections, wherein the annular electrical contact elements have an inner portion and an outer portion, wherein the inner portion defines a inner diameter defining the cavity;

injecting in a first mold containing said pin and arranged annular electrical contact elements a first material around the profiled sections so as to produce the annular isolation elements, said first material being a resiliently flexible material when solidified having a first hardness, wherein the annular isolation elements have an inner portion and an outer portion, wherein the inner portion extends into the inner diameter defining the cavity;

dimensioning said first mold so that the outside diameter of the annular isolation elements is less than the outside diameter of the annular electrical contact elements, such that the outer portion of the annular electrical contact elements extends beyond the outer portion of the annular isolation elements creating an adhesive zone defined on either side by a side on the outer portion of adjacent annular electrical contacts and a top of the outer portion of a annular isolation element between the adjacent annular electrical contacts;

injecting into a second mold containing said pin, said arranged annular electrical contact elements, and said annular isolation elements a second material around the pin so as to produce the connector head, said second material when solidified having a second hardness greater than said first hardness, said second material anchoring the annular electrical contact elements into a position and preventing movement of the annular electrical contact elements by the second material filling and extending beyond the adhesive zone; and axially releasing the pin from the cavity of the connector head thus obtained.

2. The method of claim 1 further comprising, prior to injecting the first material, bringing the annular electrical contact elements to respective determined axial positions on the smooth sections of the pin, and maintaining them in position by a positioning tool during the injection steps.

3. The method of claim 2, wherein the positioning tool comprises annular grooves formed on the outer diameter of the annular electrical contact elements and bodies for locking in position the annular electrical contact elements, cooperating with the annular grooves.

4. The method of claim 1, further comprising providing the first hardness with a hardness less than 80 Shore A.

5. The method of claim 1, further comprising providing the first material as one of an elastomer material and a thermoplastic polymer.

6. The method of claim 5, wherein the elastomer material further comprises a silicone compound.

7. The method of claim 5, wherein the thermoplastic polymer further comprises a thermoplastic polyurethane.

8. The method of claim 1, further comprising providing the second material with a hardness greater than or equal to 70 Shore D.

9. The method of claim 1, wherein the second material further comprises a thermoplastic polymer.

10. The method of claim 9, wherein the thermoplastic polymer further comprises a thermoplastic polyurethane.

11. The method of claim 1, further comprising forming an adhesion between the first material and the second material.

12. The method of claim 11, wherein the adhesion further comprises a chemical adhesion.

13. The method of claim 1, further comprising holding the annular electrical contact elements axially in place by injecting said first material and thereby forming said annular isolation elements therebetween.

\* \* \* \* \*